United States Patent [19]

Kowarski

[11] Patent Number: 5,112,804

[45] Date of Patent: May 12, 1992

[54] PHARMACEUTICAL COMPOSITION AND METHOD OF INTRANASAL ADMINISTRATION

[75] Inventor: Hanna R. Kowarski, Pikesville, Md.

[73] Assignee: Temple University of the Commonwealth System of Higher Education, Philadelphia, Pa.

[21] Appl. No.: 407,373

[22] Filed: Sep. 14, 1989

Related U.S. Application Data

[63] Continuation-in-part of Ser. No. 33,325, Apr. 1, 1987, abandoned.

[51] Int. Cl.⁵ .................. A61K 9/00; A61K 37/26; A61K 37/02
[52] U.S. Cl. .................................... 514/3; 514/4; 514/12; 514/13; 514/14; 514/15; 514/947; 514/970; 424/434
[58] Field of Search .................. 514/3, 4, 12–15, 514/947, 970; 424/434

[56] References Cited

U.S. PATENT DOCUMENTS

| | | | |
|---|---|---|---|
| 3,944,660 | 3/1976 | Gottfried et al. | 424/43 |
| 4,153,689 | 5/1979 | Hira et al. | 424/178 |
| 4,294,829 | 10/1981 | Suzuki | 424/241 |
| 4,476,116 | 10/1984 | Anik | 514/15 |
| 4,517,173 | 5/1985 | Kizawa et al. | 424/16 |
| 4,568,343 | 2/1986 | Leeper | 424/28 |
| 4,743,588 | 5/1988 | Mirejovsky | 514/24 |
| 4,764,379 | 8/1988 | Sanders | 424/449 |
| 4,820,720 | 4/1989 | Sanders | 514/356 |
| 4,835,142 | 5/1989 | Suzuki et al. | 514/53 |
| 4,865,848 | 9/1989 | Cheng | 424/449 |
| 4,873,266 | 10/1989 | Leonard | 514/653 |
| 4,888,360 | 12/1989 | Leonard | 514/675 |
| 4,888,362 | 12/1989 | Leonard | 514/724 |
| 4,933,169 | 6/1990 | Shanbrom | 424/46 |

FOREIGN PATENT DOCUMENTS

| | | |
|---|---|---|
| 128831 | 12/1984 | European Pat. Off. |
| 44-32798 | 12/1969 | Japan |
| 59-4432 | 1/1984 | Japan |
| 917575 | 2/1963 | United Kingdom |
| 1527605 | 10/1978 | United Kingdom |

OTHER PUBLICATIONS

*The Merck Index*, 11th ed., Merck and Co., 1989, Entry Nos. 3543, 4401, pp. 562 and 708.
Chemical Abstract 95:28229n (Feb. 1, 1982) abstracting Yaginuma et al. "The Influence of Anti-inflammatory Drugs on Rectal Absorption of β-lact Antibiotics", Chem. Pharmaceutical Bulletin 29 (10), 2974–89 (1981).
Medline Abstract 89258205, abstracting Mishima M. et al., "Promotion of Nasal Absorption of Insulin by Glycyrrhetinic Acid Derivatives", J. Pharmacobiodyn 12 (1), 31–6 (Jan. 1989).
Salzman et al., *Intranasal Aerosolized Insulin*, New England Journal of Medicine, pp. 1078–1084 (Apr. 25, 1985).
Gordon et al., *Nasal absorption of Insulin: Enhancement by hydrophobic bile salts*, Medical Sciences, 85 7419–7423, Nov. 1985.
Moses et al., *Insulin Administered Intranasally as an Insulin-Bile Salt Aerosol*, Diabetes 32, 1040–1047, Nov. 1983.
Hirai, *The International Journal of Pharmaceuticals*, 9, 165–172 (1981).
*The Merck Index*, 9th ed., Merck & Co., Inc., 1976, entry Nos. 470 and 4369, p. 647.
Pontiroli, *British Medical Journal* 284, 303–306 (1982).
Fieser & Fieser, *Organic Chemistry* (3rd Ed.), Reinhold Pub. Co. N.Y., N.Y. 113–115, 218, 353, 607, 622, 628, 635, 681–684 (1956).
Finar, *Organic Chemistry*, vol. 2, (6th Ed.), Longman, N.Y., N.Y., Chap. 1, pp. 4–5.
Hermens et al., *Pharmaceutical Research*, vol. 4, No. 6, 445–449, (1987).

*Primary Examiner*—F. T. Moezie
*Attorney, Agent, or Firm*—Seidel, Gonda, Lavorgna & Monaco

[57] ABSTRACT

A composition and method for nasal administration of pharmaceuticals utilizes glycyrrhetinic acid as an absorption enhancer. The composition comprises an effective amount of the pharmaceutically active substance, glycyrrhetinic acid, in an amount effective for enhancing permeation of the active substance across the nasal membrane, and a basic salt of an amino acid as an adjuvant. The composition may be administered to the nasal cavity in the form of a spray by using an atomizer, nebulizer, spayer, dropper or other device which ensures contact of the composition with the nasal mucus membrane.

32 Claims, 14 Drawing Sheets

PHARMACEUTICAL COMPOSITION AND METHOD OF INTRANASAL ADMINISTRATION

CROSS-REFERENCE TO RELATED APPLICATION

This is a continuation-in-part of co-pending patent application Ser. No. 033,325, filed Apr. 1, 1987, now abandoned.

FIELD OF THE INVENTION

The invention relates to a novel composition and method for the intranasal administration of pharmaceutical substances.

BACKGROUND OF THE INVENTION

Systemically active drugs have been administered by a wide variety of routes, such as orally, rectally, vaginally, subcutaneously, intramuscularly, intravenously, etc.

Some pharmaceuticals, peptide drugs in particular, are not suitable for oral administration. For these drugs, parenteral administration is the only alternative.

The traditional mode of administration of insulin is by subcutaneous injection. Control of diabetes mellitus often requires multiple injections each day, which are painful and distressing to many patients.

Discomfort and destruction of lifestyle often deter diabetics from accepting intensive insulin treatment. For these reasons, attention has been focused on alternative routes of administration of insulin and other chronically-needed medicaments.

Attempts have been initiated to administer insulin enterally, with and without liposome encapsulation, vaginally, and through the respiratory epithelium. Because of the limited absorption of insulin, these attempts have largely failed.

A great deal of interest has been focused on the intranasal mode of administration of drugs. Vasopressin, luteinizing hormone releasing factor ("LHRF"), adrenocorticotrophic hormone ("ACTH"), and in particular insulin, have been administered intranasally. While intranasal administration offers advantages over other routes, many drugs exhibit only limited absorption through the nasal mucosa. For example, insulin, when administered intranasally, neither increases serum insulin levels nor lowers blood glucose concentration. To be absorbed from the nasal mucosa to reach the blood circulation, the pharmaceutical molecules must be transported across nasal mucous membranes by means of an absorption enhancer.

Many agents have been suggested as intranasal absorption enhancers. U.S. Pat. No. 4,476,116 discloses pharmaceutical compositions for intranasal delivery including chelating agents which enhance absorption across the nasal mucous membranes. U.S. Pat. No. 4,153,689 discloses insulin preparations for intranasal administration containing one or more non-ionic surface-active agents as an absorption enhancer. Bile salts such as sodium deoxycholate have also been used to increase intranasal insulin absorption. Moses et al., *Diabetes* 32:1040–1047 (1983); Gordon et al., *Proc. Natl. Acad. Sci. USA* 82:7419 (1985). However, bile salts are undesirable since they cause nasal irritation and damage to the nasal mucosa. While much attention has been devoted to intranasal insulin formulations containing non-ionic surfactant enhancers such as laureth-9 (polyoxethylene-9-laurylether), such surfactants cause nasal stinging, congestion and rhinorrhea. Salzman et al., *N. Eno. J. Med.* 312:1078–1084 (1985).

What is needed is an effective enhancing agent for the transport of pharmaceutically active substances across the nasal membrane which is free of the irritation and other undesirable side effects experienced with presently-used intranasal delivery formulations.

SUMMARY OF THE INVENTION

A composition for the intranasal administration of a pharmaceutically active substance is provided. The composition comprises an effective amount of the pharmaceutically active substance, glycyrrhetinic acid in an amount effective for enhancing permeation of the active substance across the nasal membrane, and a basic salt of an amino acid as an adjunct. A method for administering pharmaceutically active substances by intranasal administration is also provided.

DESCRIPTION OF THE FIGURES

FIG. 3 is a plot of the blood glucose concentration of an animal subject as a function of time after nasal administration of 0.1 ml of an insulin preparation according to Example 3a.

FIG. 4 is a plot of the blood glucose concentration of an animal subject as a function of time after nasal administration of 0.2 ml of an insulin preparation according to Example 3a.

DETAILED DESCRIPTION OF THE INVENTION

Figure 1:
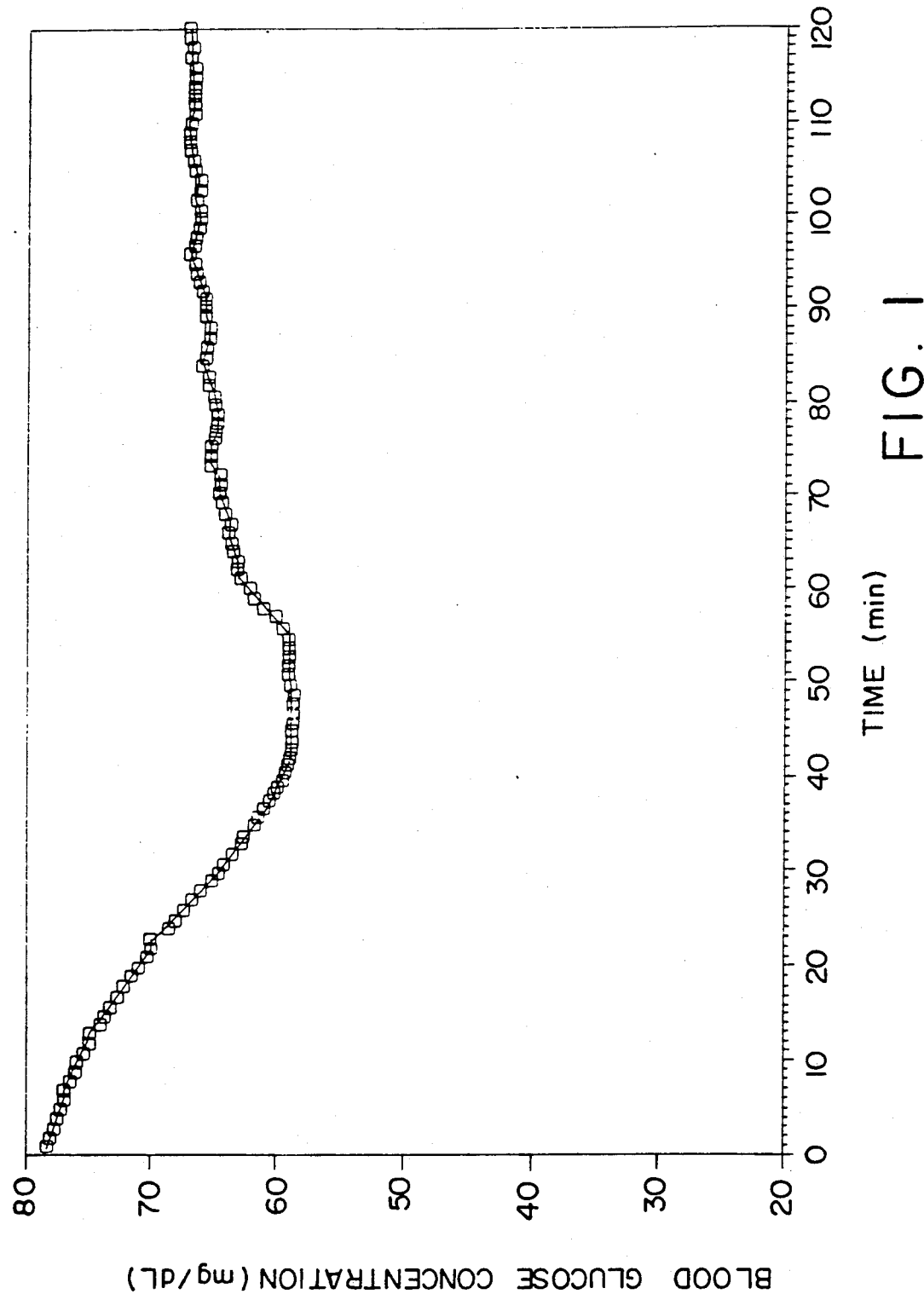
FIG. 1 is a plot of the blood glucose concentration of an animal subject as a function of time after nasal administration of 0.1 ml. of an insulin preparation according to Example 1.

Glycyrrhetinic acid, the aglycone of glycyrrhizin, may exist in a number of isomeric forms, two of which are known as 18α- and 18β-glycyrrhetinic acid. I have found surprisingly that glycyrrhetinic acid when combined with a pharmaceutically active substance, significantly enhances permeation of the active substance across the nasal membrane without the deleterious side effects of known nasal absorption enhancing agents.

Pharmaceutically active substances which may be prepared for nasal administration in this manner include all manner of biologically active agents, which may have utility in the treatment or prevention of disease or disorders affecting animals and/or humans, or in the regulation of any animal or human physiological condition. Such agents include, for example, hormones such as insulin, growth hormone, growth hormone releasing factor, glucagon, somatostatin, chorionic gonadotropin, adrenocorticotropic hormone (ACTH), and interferon; steroids such as prednisone, prednisolone, hydrocortisone, triamcinolone, dexamethasone and betamethasone; antiinflammatory agents such as aspirin, aminopyrine, acetaminophen, ibufenac, ibuprofen, indomethacin, colchicine, sulpyrine, mefenamic acid, phenacetin, phenylbutazone, flufenamic acid and probenecid; antihistamine agents such as diphenhydramine hydrochloride and dexchlorpheniramine maleate; antibiotics such as penicillin or its derivatives, cephalosporin or its derivatives; erythromycin, tetracycline, furadiomycin, leucomycin; chemotherapeutic agents such as sulfathiazole and nitrofurazone; cardiac agents such as digitalis and digoxin; blood vein dilating agents such as nitroglycerin and papaverine hydrochloride; cough curing agents such as codeine; azulen; phenovalin; pepsin; enzymes such as lysozyme hydrochloride; other systemic agents such as antihypertensives and diuretics; tranquilizers; sex hormones; vitamins; and ulcer medications.

Other such pharmaceutically active agents are known to those skilled in the art.

The intranasal delivery composition is particularly well suited for the following pharmaceuticals presently marketed or under investigation for nasal delivery: vasopressin, oxytocin, luteinizing hormone releasing factor (LHRF), calcitonin, auriculin, flu vaccine and other vaccines, thyrotrophin releasing hormone (TRH), progesterone, propanolol, metoclopramide, narcotic analgesics, vitamin $B_{12}$ and antihistamines.

The intranasal delivery composition is particularly well-suited for the administration of polypeptides having systemic activity, such as, for example, any of the polypeptides appearing in the preceding paragraphs.

The intranasal delivery composition is most particularly well-suited for the administration of insulin. Insulin may be of the animal type, such as porcine or bovine insulin. Human insulin, such as prepared by recombinant DNA techniques, may also be used. A method for treating diabetes mellitus therefore comprises administering through the nasal mucous membrane of a patient suffering from diabetes an effective amount of an aqueous insulin solution according to the present invention which contains an amount of insulin effective in inducing regulation of blood glucose level.

Any isomer of glycyrrhetinic acid may be used in the compositions of the present invention, although the 18α- and 18β- isomers, or mixtures thereof, are preferred. 18β-glycyrrhetinic acid is particularly preferred. The compositions of the present invention containing glycyrrhetinic acid have no bitter taste or after-effects in small doses, unlike prior art intranasal compositions relying on surfactant or bile salt enhancers.

The composition contains one or more basic salts of an amino acid, as an adjuvant to aid in the dissolution of the glycyrrhetinic acid component of the composition. Amino acids may be conveniently converted to their basic salts by treatment with an appropriate base, such as potassium hydroxide or sodium hydroxide. Suitable amino acid basic salts include, for example, the sodium or potassium salts of glycine, aspartatic acid, and glutamic acid. Either the levo, dextro or racemic forms of the amino acids may be employed. Thus, useful basic salts of amino acids for use in the present compositions include, for example, sodium glycinate, monosodium aspartate, monosodium L-glutamate, monopotassium L-aspartate, monopotassium D,L-aspartate, and other basic salts of amino acids.

The pharmaceutical substance, glycyrrhetinic acid in an amount effective to enhance absorption of the pharmaceutical substances by permeation across the nasal membrane, and the basic amino acid salt, may be dissolved in an aqueous diluent. Water may be used as the diluent. Alternatively, the diluent may comprise an aqueous buffer such as phosphate buffer.

A phosphate buffer, pH 7.6 useful as a diluent may be prepared by combining 2.5 ml of 0.02 M $KH_2PO_4$ and 2.12 ml of 0.02 M NaOH, and adding $H_2O$ up to a final volume of 10.0 ml.

The amount of glycyrrhetinic acid combined with the pharmaceutically active substance is any amount sufficient to increase the active substance's permeability across the nasal membrane of an animal or human.

Generally, a concentration of glycyrrhetinic acid of about 0.25 to about 1.5% (w/v) in the composition will be sufficient to obtain an acceptable absorption enhancement across the nasal membrane. A higher or lower glycyrrhetinic acid concentration may be required, depending on the nature and dose of the pharmaceutical substance being administered. However, above about 1.5% (w/v), the composition may begin forming a gel, which may retard release of the active agent and absorption enhancer. Preferably, the concentration of glycyrrhetinic acid ranges from about 0.5 to about 1.0% (w/v).

The concentration of amino acid basic salt is selected to promote the dissolution of the glycyrrhetinic acid. The amount is preferably selected to establish, on a molar basis, a ratio of amino acid salt to glycyrrhetinic acid of from about 1:1 to about 5:1. A higher or lower concentration of amino acid basic salt may be utilized.

The amount of the pharmaceutically active substance contained in the composition may, of course, vary depending on a variety of factors. Chief among these is the nature of the active substance. By "effective amount" of the active substance is meant herein an amount sufficient to achieve and maintain therapeutic blood levels of that substance in an animal (including human) subject over a desired period of time. The specific amounts utilized will, of course, vary with the nature of the active substance, and its potency; the amount required to bring about the desired therapeutic or other effect; the role of elimination or breakdown of the agent; the size, weight and condition of the subject; and the amount of the glycyrrhetinic acid absorption enhancer in the preparation. The selection of the approximate amount of active substances for nasal administration is within the capability of the skilled artisan, by routine optimization. Appropriate dosages for intranasal administration are further apparent to one skilled in the art, as is apparent from a consideration of prior nasal delivery enhancement systems, such as those described in U.S. Pat. Nos. 4,746,508; 4,476,116; and 4,153,689.

The composition may further optionally include one or more polyhydric alcohols to increase the solubility of glycyrrhetinic acid. Such polyhydric alcohols include, for example, propylene glycol, glycerin, polyethylene glycol, and sorbitol. A hydroxide, e.g., NaOH, may also be added when needed to increase the alkalinity of the formulation to promote dissolving of glycyrrhetinic acid.

Finally, the composition may optionally include one or more preservative agents such as, for example, gentamicin, bacitracin (0.005%), or cresol.

The preparations of the invention may be produced by mixing the ingredients in any order by conventional means, taking care that the glycyrrhetinic acid becomes dissolved in the diluent. The composition of the invention is generally in the form of a liquid solution in which the glycyrrhetinic acid is at least partially, and preferably completely, dissolved in the diluent. Thus, it is contemplated that the composition is advantageously prepared in the form of a saturated, unsaturated or supersaturated solution. It is believed that when in solution form, the effect of the glycyrrhetinic acid in enhancing nasal absorption is maximized.

The compositions may be administered to the nasal cavity in the form of a spray by using an atomizer, nebulizer, sprayer, dropper or other device which insures contact of the solution with the nasal mucous membrane.

The practice of the present invention is illustrated by the following non-limiting examples. For preparations containing human insulin, a commercially available human insulin solution containing 100 units/ml and 0.2% (w/v) phenol was utilized as a source of insulin. Unless stated otherwise, each preparation contains 1% (w/v) glycyrrhetinic acid.

EXAMPLE 1

100.5 mg 18α-glycyrrhetinic acid are mixed in a test tube with 1 ml of a solution of 501 mg sodium glycinate in 10 ml of 0.02 M phosphate buffer (prepared by combining 2.5 ml 0.02 M $KH_2PO_4$ and 2.12 ml 0.02 M NaOH, and adding water up to a final volume of 10.0 ml). The mixture is stirred with a glass rod and heated to 90°–100° C. to dissolve the glycyrrhetinic acid by immersing the test tube in a water bath of boiling water for about 5 min. Stirring may continue until the mixture becomes homogenous. Following removal from the hot water bath, 1.0 ml of propylene glycol is added, followed by 5 drops from a solution of 502 mg glycine HCl in 10 ml of 0.02 M phosphate buffer. 0.02 M phosphate buffer is then added to raise the solution to a volume of 5 ml. One ml of this nasal absorption-enhancing solution is mixed with 1 ml of a 100 unit/ml commercially-available human insulin solution (Squib-Novo). The resulting preparation contains 50 units of insulin per ml.

EXAMPLE 2

To 106.5 mg 18α-glycyrrhetinic acid are added 1 ml of a solution of 502 mg sodium glycinate in 10 ml of 0.02 M phosphate buffer followed by mixing and heating as in Example 1. 5 ml of propylene glycol are then added, followed by 0.02 M phosphate buffer to 5 ml. 2.5 ml of this solution are added to 2.5 ml of a 100 unit/ml solution of human insulin. The insulin concentration in this final preparation is 50 units/ml.

EXAMPLE 3a

To 100.5 mg 18β-glycyrrhetinic acid are added 10 ml of a solution containing 100.5 mg sodium glycinate per ml of distilled water, followed by mixing and heating as in Example 1. 1 ml glycerin is then added, followed by water up to 5 ml. 2 ml of this preparation are added to 2 ml of a human insulin solution of 100 units per ml to yield a final insulin preparation of 50 units per ml insulin.

EXAMPLE 3b

The preparation of Example 3a is repeated except the amount of glycyrrhetinic acid is reduced to 0.5% (w/v).

EXAMPLE 3c

The preparation of Example 3a is repeated except the concentration of glycyrrhetinic acid is reduced to 0.25% (w/v).

EXAMPLE 4

To 200.5 mg 18β-glycyrrhetinic acid are added 1.5 ml of a solution of 1005 mg sodium glycinate in 10 ml water, followed by mixing and heating as in Example 1. 1 ml of glycerin is then added. 2 ml of this preparation is combined with 2 ml of a human insulin solution containing 100 units per ml of insulin, which yields a final preparation containing 50 units of insulin per ml.

EXAMPLE 5

50 mg sodium glycinate are added to 0.5 ml of 0.02 M phosphate buffer and 50 mg of 18β-glycyrrhetinic acid and mixed until liquid. 0.5 ml of glycerin is then added. 50 mg of insulin crystals (24 units per mg) are dissolved in 1 ml of 0.1 N HCl, which is then added to the above mixture. Addition of phosphate buffer up to 5 ml provides a final preparation containing 240 units of insulin per ml.

EXAMPLE 6

0.5 ml of glycerin and 2 ml of water are added to 2.5 ml of the final preparation from Example 4. 5 ml of the resulting solution is combined with 5 ml of a human insulin solution of 500 units per ml. The final preparation contains 250 units of insulin per ml and 0.5% (w/v) of 18β-glycyrrhetinic acid.

EXAMPLE 7

To 90.5 mg of 18β-glycyrrhetinic acid are added 1 ml of a solution consisting of 504 mg L-aspartic acid monosodium salt per ml of water. Following mixing and heating as in Example 1, 0.2 ml of 1 N NaOH, 1 ml of glycerin, and water up to 5 ml are added. The resulting solution is added to 5 ml of an aqueous human insulin solution containing 100 units of insulin per ml to yield a final preparation containing 50 units of insulin per ml.

EXAMPLE 8

2 ml of a solution of 501.5 mg L-glutamic acid monosodium salt in 10 ml water are added to 100 mg 18β-glycyrrhetinic acid, and mixed and heated as in Example 1. 0.4 ml of 1N NaOH, 1 ml of glycerin and water up to 5 ml are then added. 5 ml of a human 100 unit/ml insulin solution are added to yield a final insulin preparation of 50 units per ml.

EXAMPLE 9

1 ml of a solution of 510 mg L-aspartic acid monopotassium salt in 10 ml water is added to 100.5 mg 18β-glycyrrhetinic acid, followed by mixing and heating as in Example 1. 0.2 ml 1 N NaOH solution, 1 ml of glycerin and water up to 5 ml are then added. This solution is combined with 5 ml of a human insulin solution containing 100 units insulin per ml. The final preparation contains 50 units of insulin per ml.

EXAMPLE 10

To 100.5 mg 18β-glycyrrhetinic acid are added 1 ml of a solution containing 510 mg D,L-aspartic acid monopotassium salt in 10 ml water, followed by mixing and heating as in Example 1. 0.2 ml 1N NaOH, 1 ml of glycerin and water up to 5 ml are then added. This solution is mixed with 5 ml of a human insulin solution containing 100 units per ml insulin to provide a final preparation containing 50 units of insulin per ml.

COMPARATIVE EXAMPLE 11

1 ml of 100 unit/ml human insulin solution was mixed with 1 ml of distilled water. This diluted solution containing 50 units/ml insulin was used as a control.

COMPARATIVE EXAMPLE 12

1 ml of a human insulin solution containing 100 units/ml of insulin were mixed with 1 ml of phosphate buffer, pH 7.6. The diluted solution of 50 units/ml insulin was used as a control.

COMPARATIVE EXAMPLE 13

A sham preparation was prepared according to Example 3a, but omitting the insulin.

The hypoglycemic effect of the above preparations was confirmed in animal glucose monitoring studies utilizing continuous glucose monitoring with the device described in *J. Clin. Endocrinol. Metab.* 53: 1145 (1984). The device consists of a system for nonthrombogenic blood withdrawal coupled to a system for blood glucose measurement. The blood withdrawal system includes a disposable sterile intravenous needle and catheter connected to a peristaltic pump. The inside wall of the catheter is coated with tridodecylmethylammonium chloride complexed with heparin to provide a nonthrombogenic surface. Blood is continuously withdrawn at a rate of 12 ml/hr from the experimental animal via the nonthrombogenic catheter. The blood is diluted in a Plexiglass mixing chamber with six volumes of phosphate buffer solution (0.015 M; pH 7.4) containing 10 IU/ml heparin and then moved into the device's sensory chamber. The sensory chamber contains a glucose-sensing system comprising a glucose sensing probe, a digital display and a digital graphic recorder.

INSULIN ABSORPTION ANIMAL STUDY

Six preconditioned female mongrel hound dogs treated for worms, weighing 19-20 kg, were fasted overnight and anesthetized in the morning with intravenous "NEMBUTAL" sodium pentobarbital (250 mg initial dose, 25 mg every 30 minutes for maintenance). Continuous glucose monitoring was then initiated, using the device described above, upon inserting the catheter into one of the major veins of the animal's front leg. A medicine dropper was inserted through the nasal opening into the nasal cavity. A plastic tubing was inserted through the medicine dropper into the nasal cavity. A preparation according to one of the above Examples was administered by injection into the plastic tubing with a small syringe. The solution was then blown into the nasal cavity of the animal. Blood glucose level was continuously monitored. The resulting decrease in blood glucose level for the insulin dosages in Table 1 are recorded in FIGS. 1 to 12.

TABLE 1

| Example | Amount of Preparation (ml) | Insulin Dose Units | FIG. |
|---------|---------------------------|---------------------|------|
| 1       | 0.1                       | 5                   | 1    |
| 2       | 0.1                       | 5                   | 2    |
| 3a      | 0.1                       | 5                   | 3    |
| 3a      | 0.2                       | 10                  | 4    |
| 3b      | 0.2                       | 10                  | 5    |
| 3c      | 0.2                       | 10                  | 6    |
| 8       | 0.2                       | 10                  | 7    |
| 10      | 0.2                       | 10                  | 8    |
| 11      | 0.1                       | 5                   | 9    |
| 11      | 0.2                       | 10                  | 10   |
| 12      | 0.1                       | 5                   | 11   |
| 13      | 0.2                       | —                   | 12   |

Figure 12:
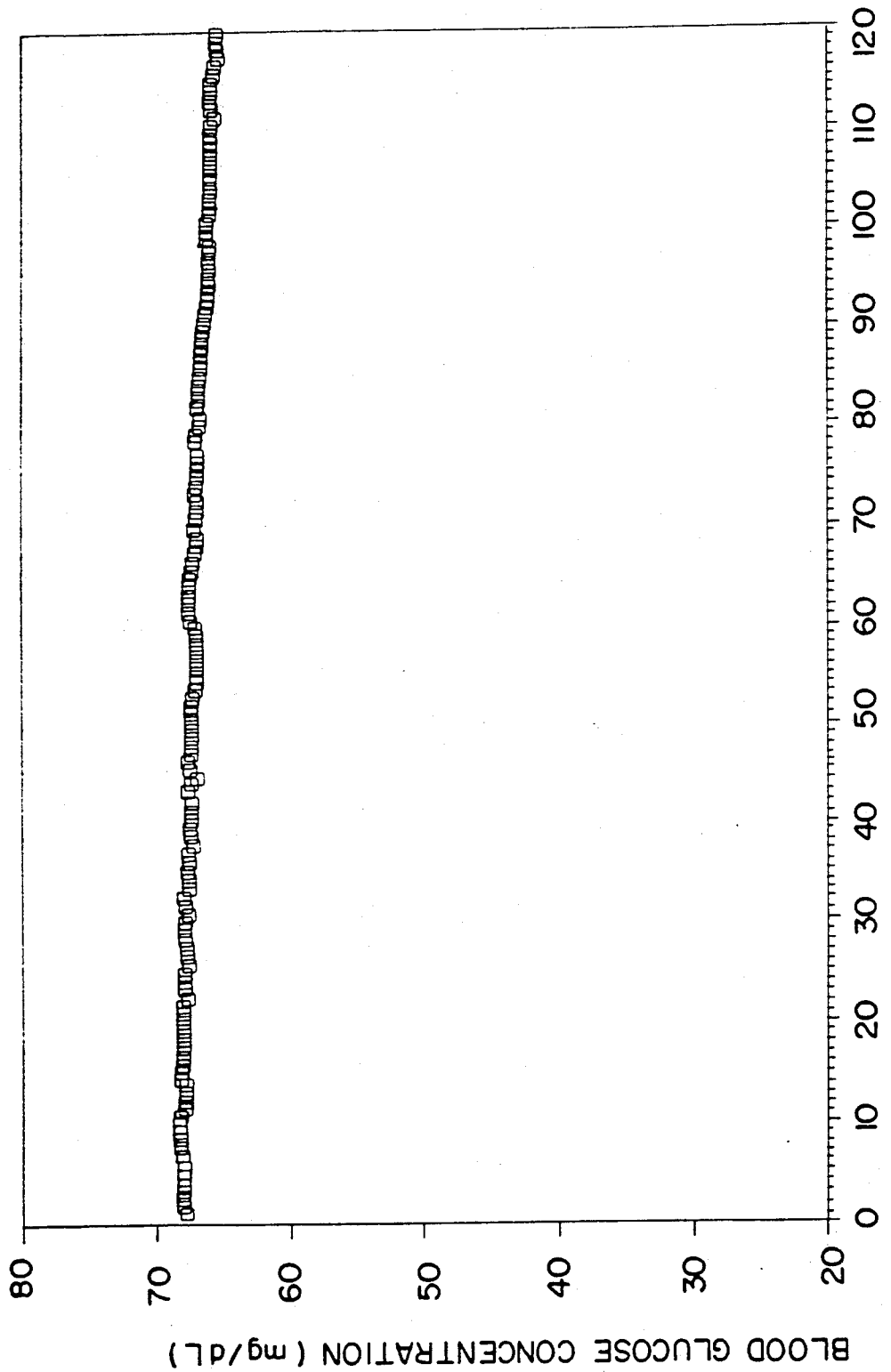
FIG. 12 is a plot of the blood glucose concentration of an animal subject as a function of time after nasal administration of 0.2 ml of an insulin preparation according to Example 13.

The effectiveness of the insulin preparation of the invention is indicated by a substantial decrease in blood glucose level (FIGS. 1-8) in relation to the comparative examples lacking either glycyrrhetinic acid (FIGS. 9-11) or insulin (FIG. 12). The results indicate that glycyrrhetinic acid is effective in enhancing absorption of insulin across the nasal membrane.

Figure 2:
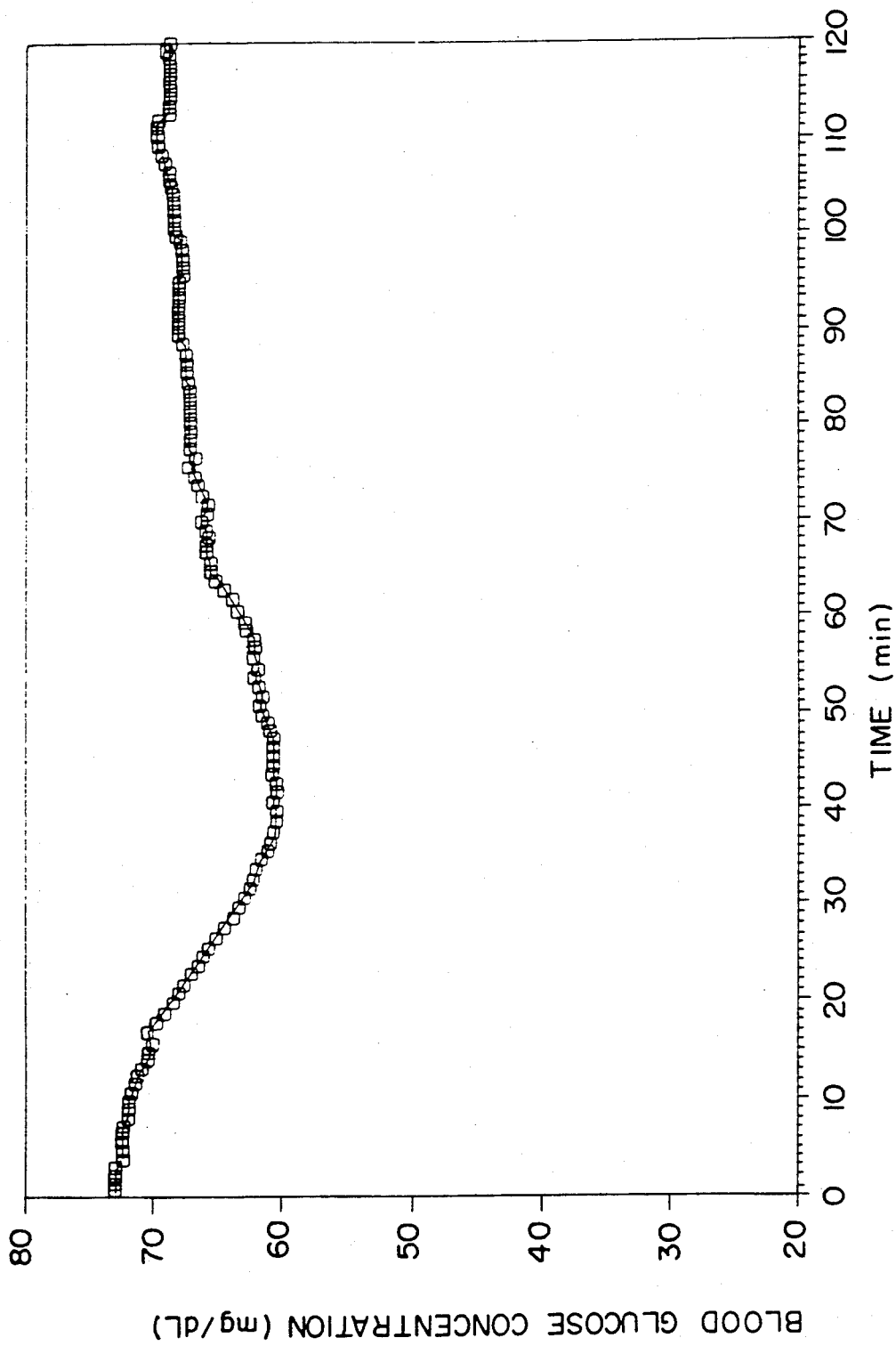
FIG. 2 is a plot of the blood glucose concentration of an animal subject as a function of time after nasal administration of 0.1 ml of an insulin preparation according to Example 2.
Figure 3:
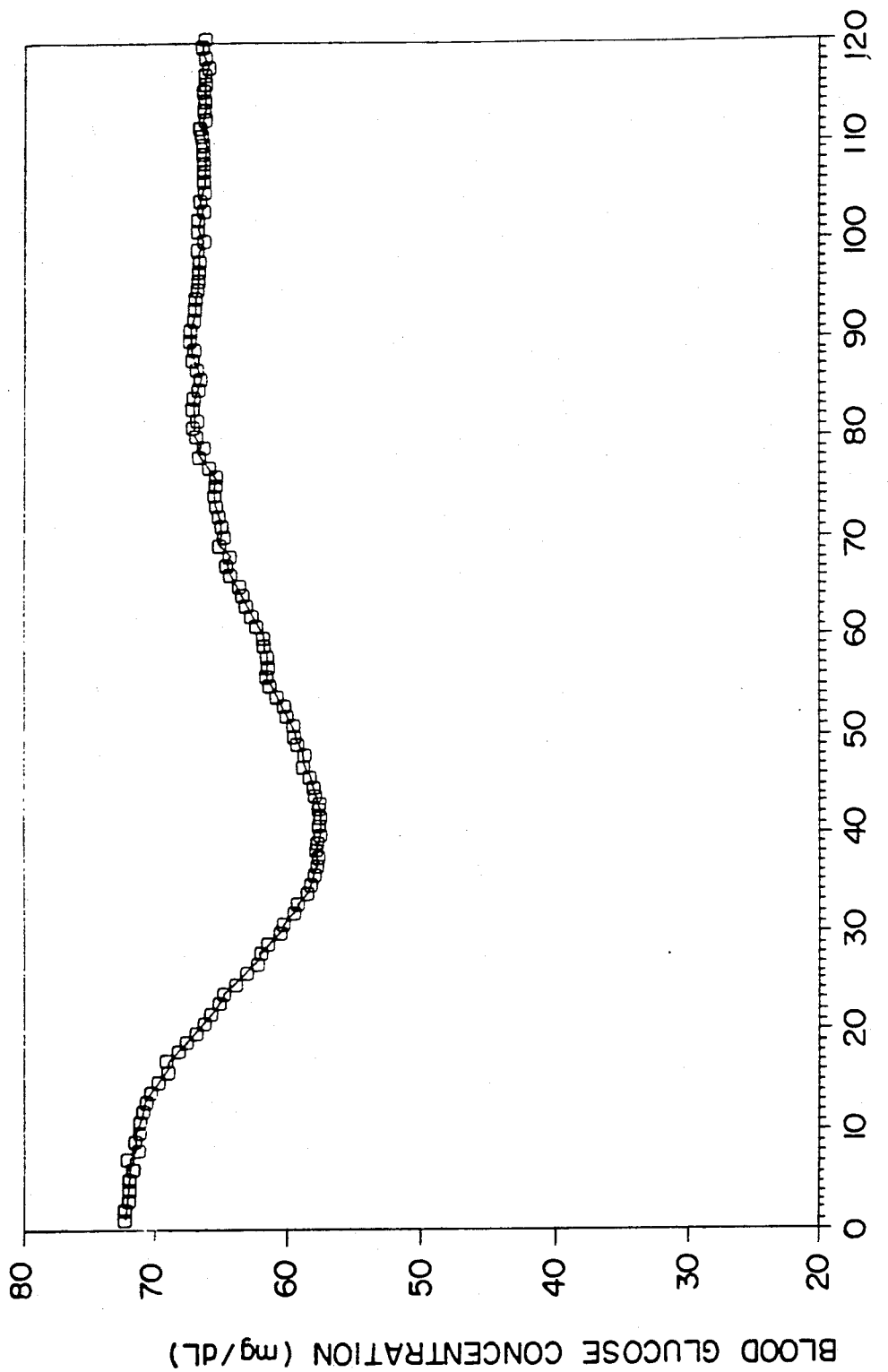
Figure 4:
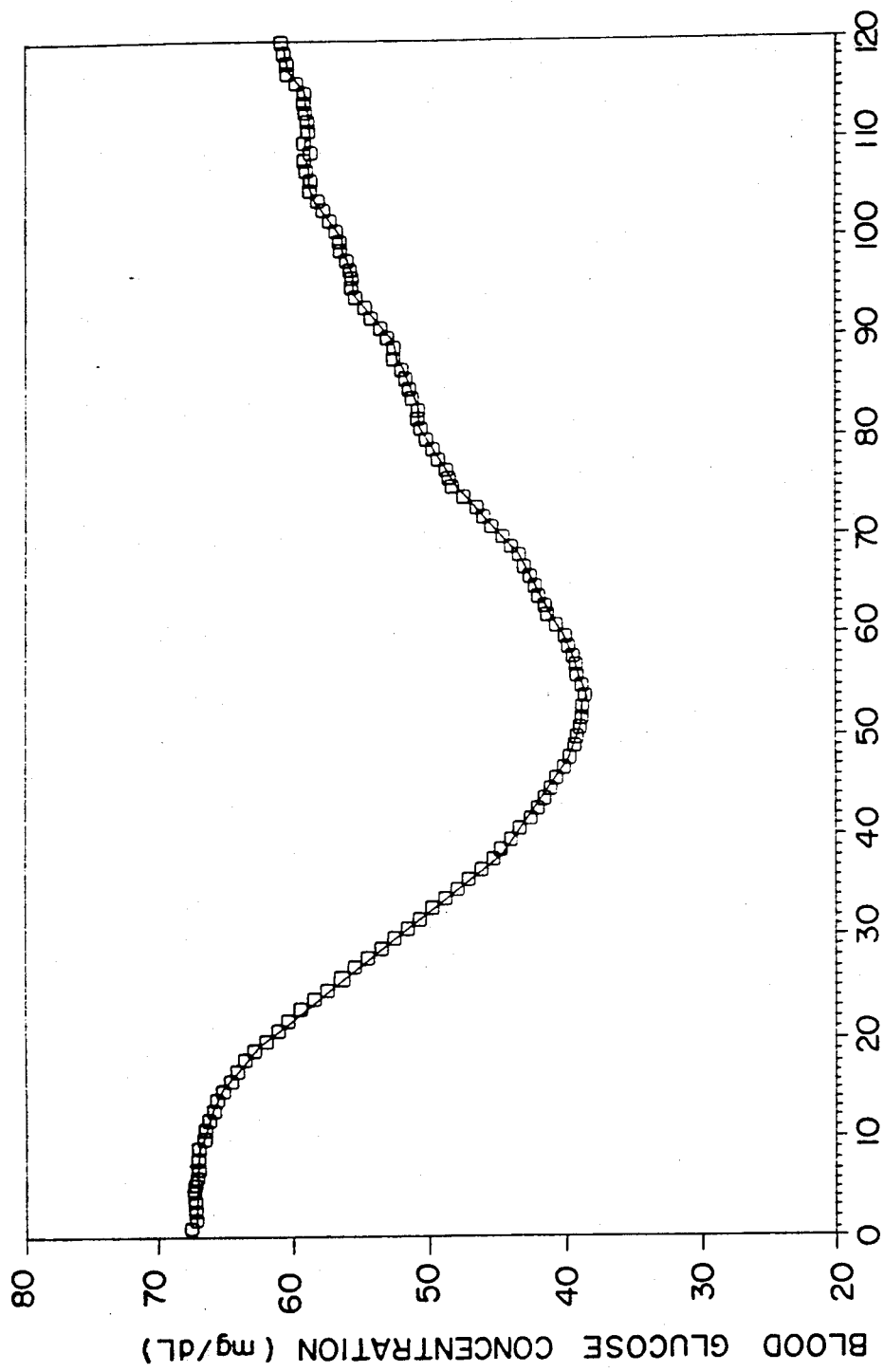
Figure 5:
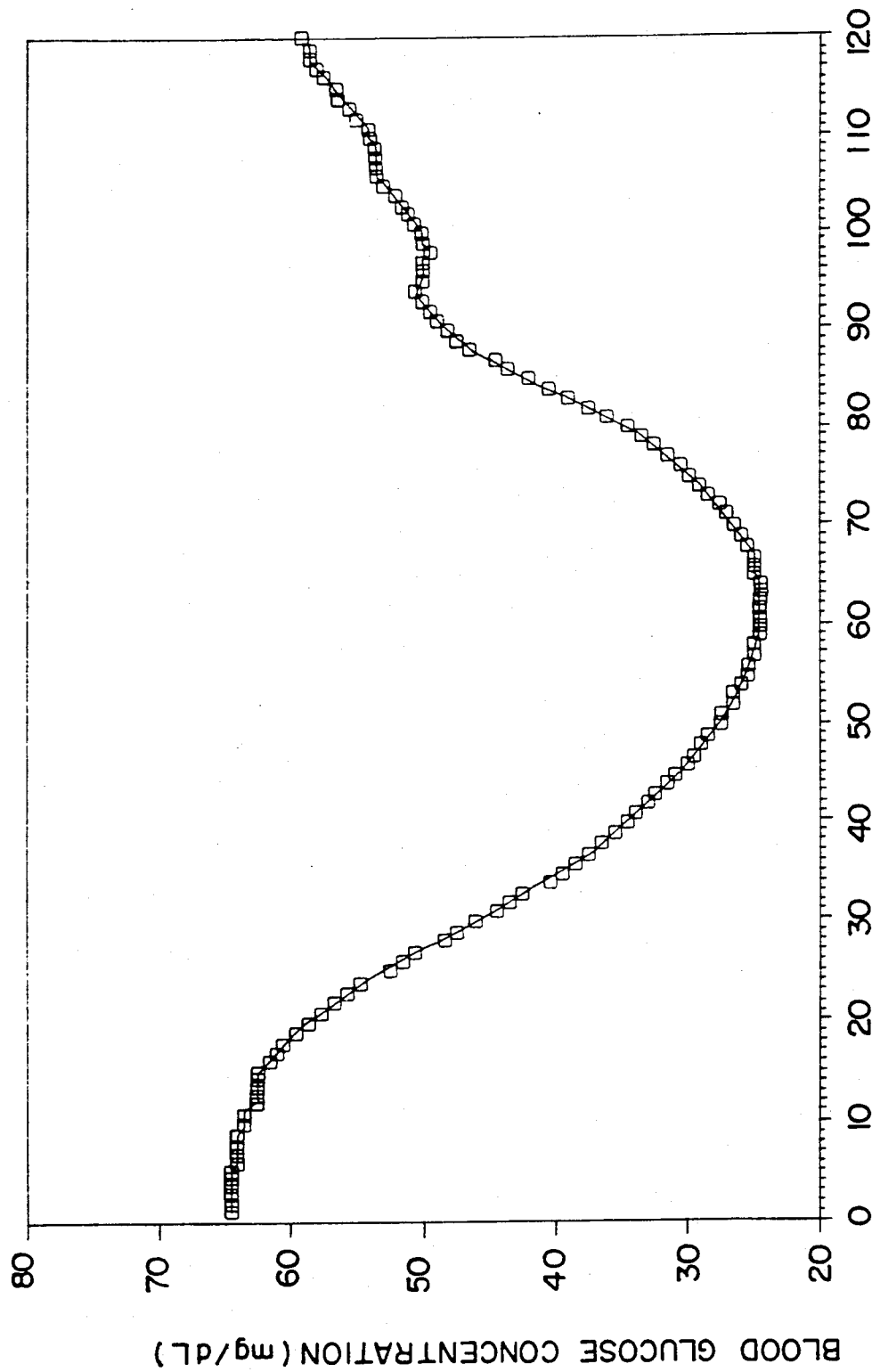
FIG. 5 is a plot of the blood glucose concentration of an animal subject as a function of time after nasal administration of 0.2 ml of an insulin preparation according to Example 3b.
Figure 6:
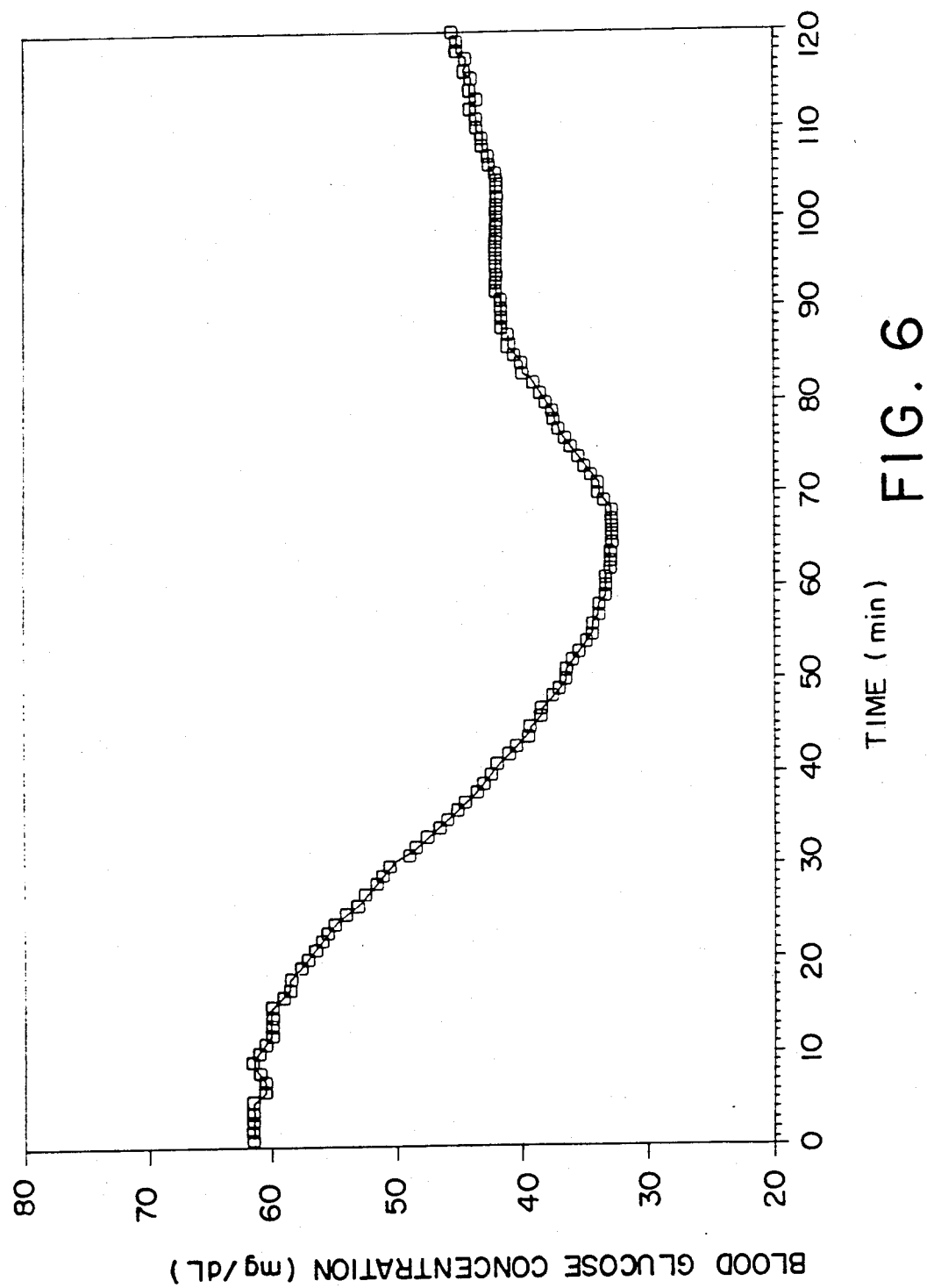
FIG. 6 is a plot of the blood glucose concentration of an animal subject as a function of time after nasal administration of 0.2 ml of an insulin preparation according to Example 3c.
Figure 7:
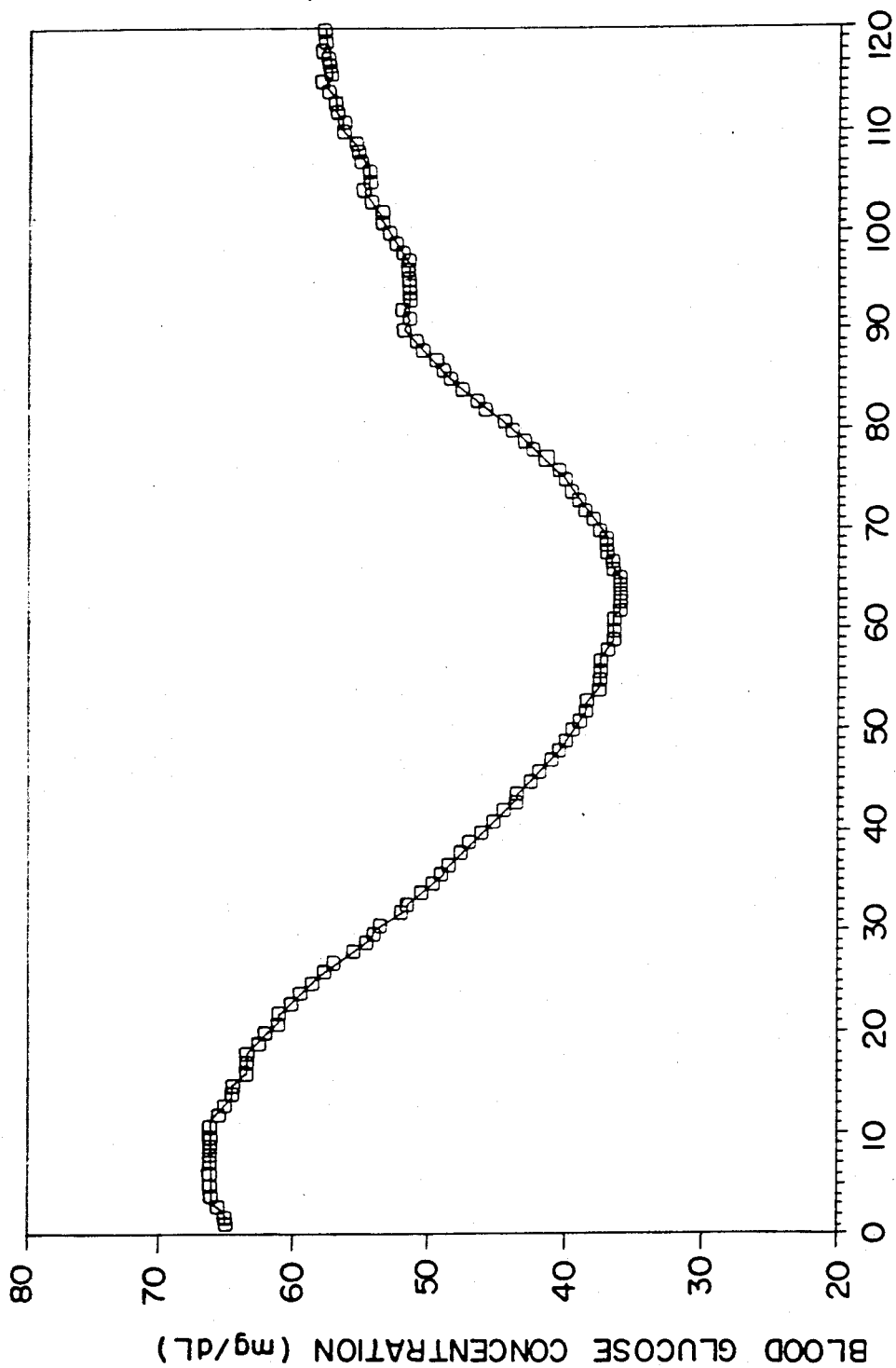
FIG. 7 is a plot of the blood glucose concentration of an animal subject as a function of time after nasal administration of 0.2 ml of an insulin preparation according to Example 8.
Figure 8:
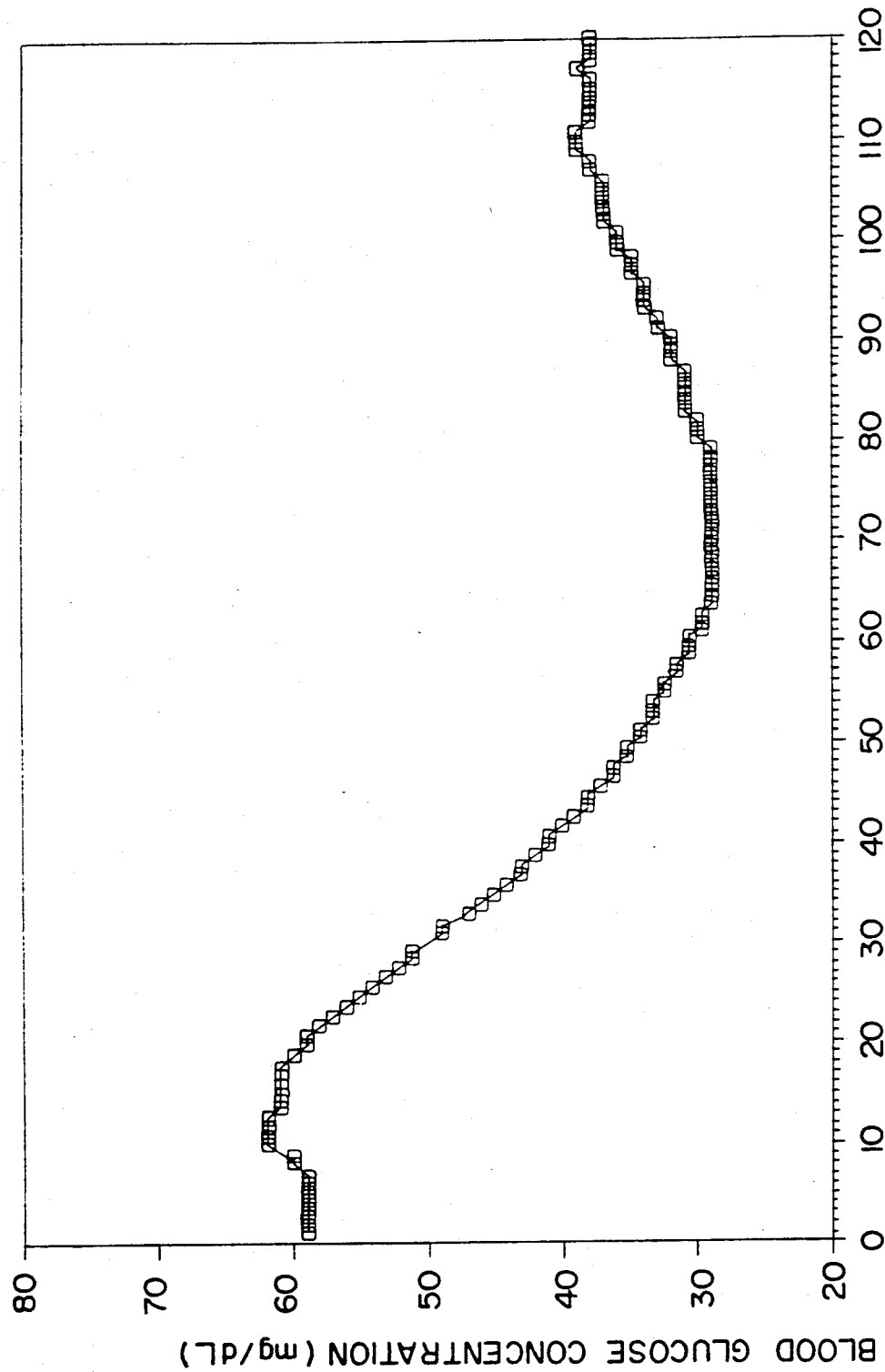
FIG. 8 is a plot of the blood glucose concentration of an animal subject as a function of time after nasal administration of 0.2 ml of an insulin preparation according to Example 10.
Figure 9:
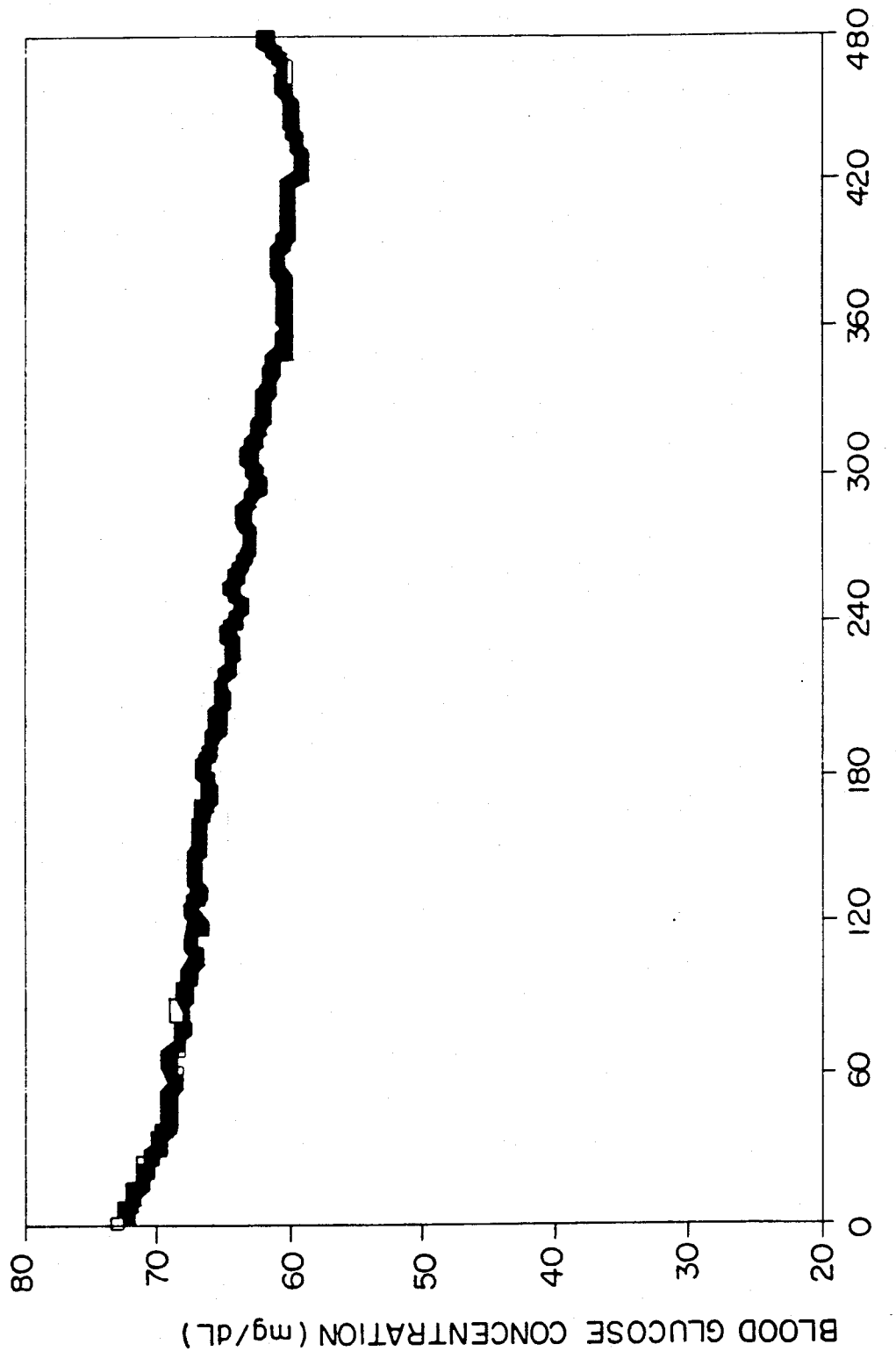
FIG. 9 is a plot of the blood glucose concentration of an animal subject as a function of time after nasal administration of 0.1 ml of an insulin preparation according to Example 11.
Figure 10:
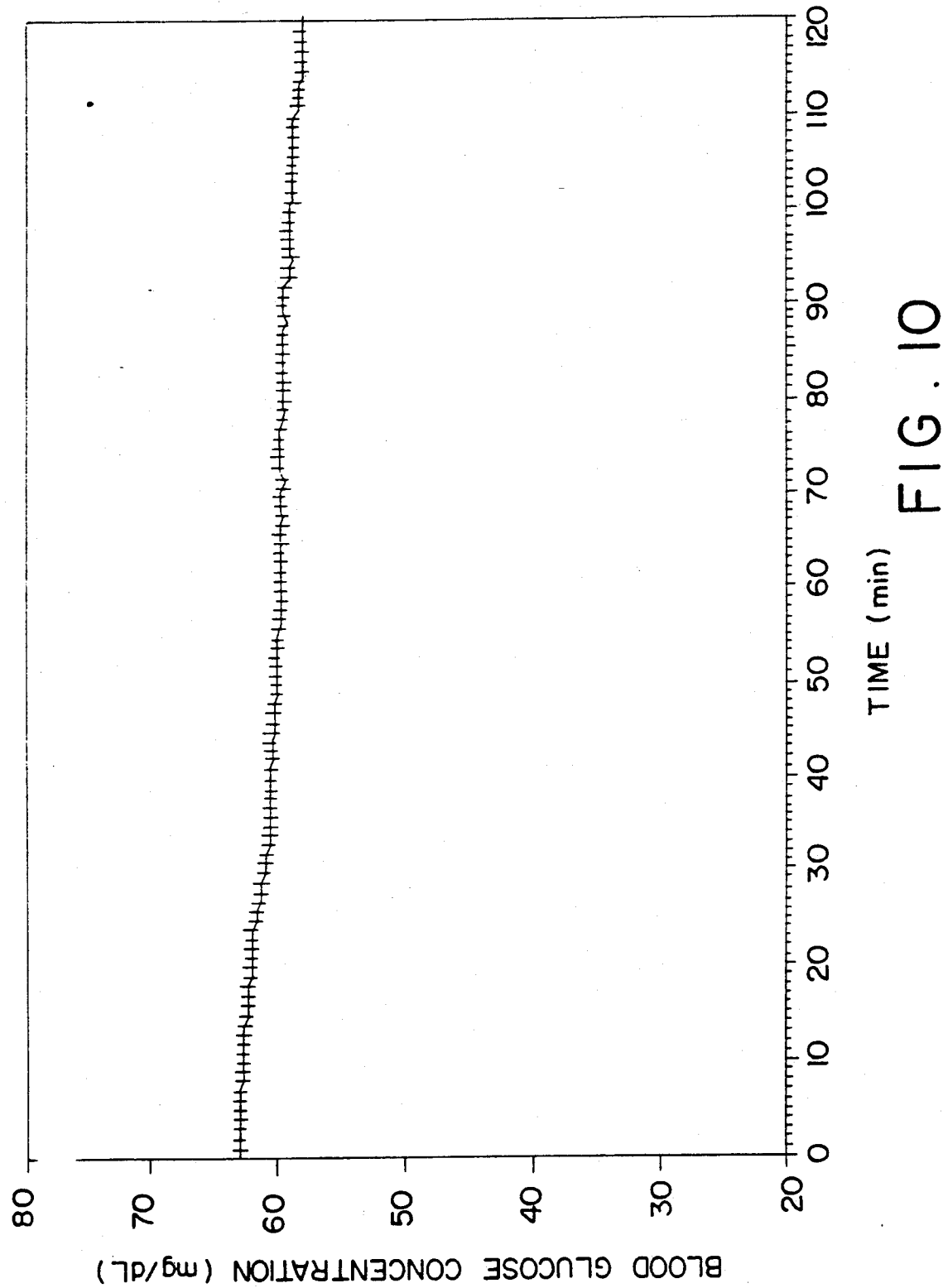
FIG. 10 is a plot of the blood glucose concentration of an animal subject as a function of time after nasal administration of 0.2 ml of an insulin preparation according to Example 11.
Figure 11:
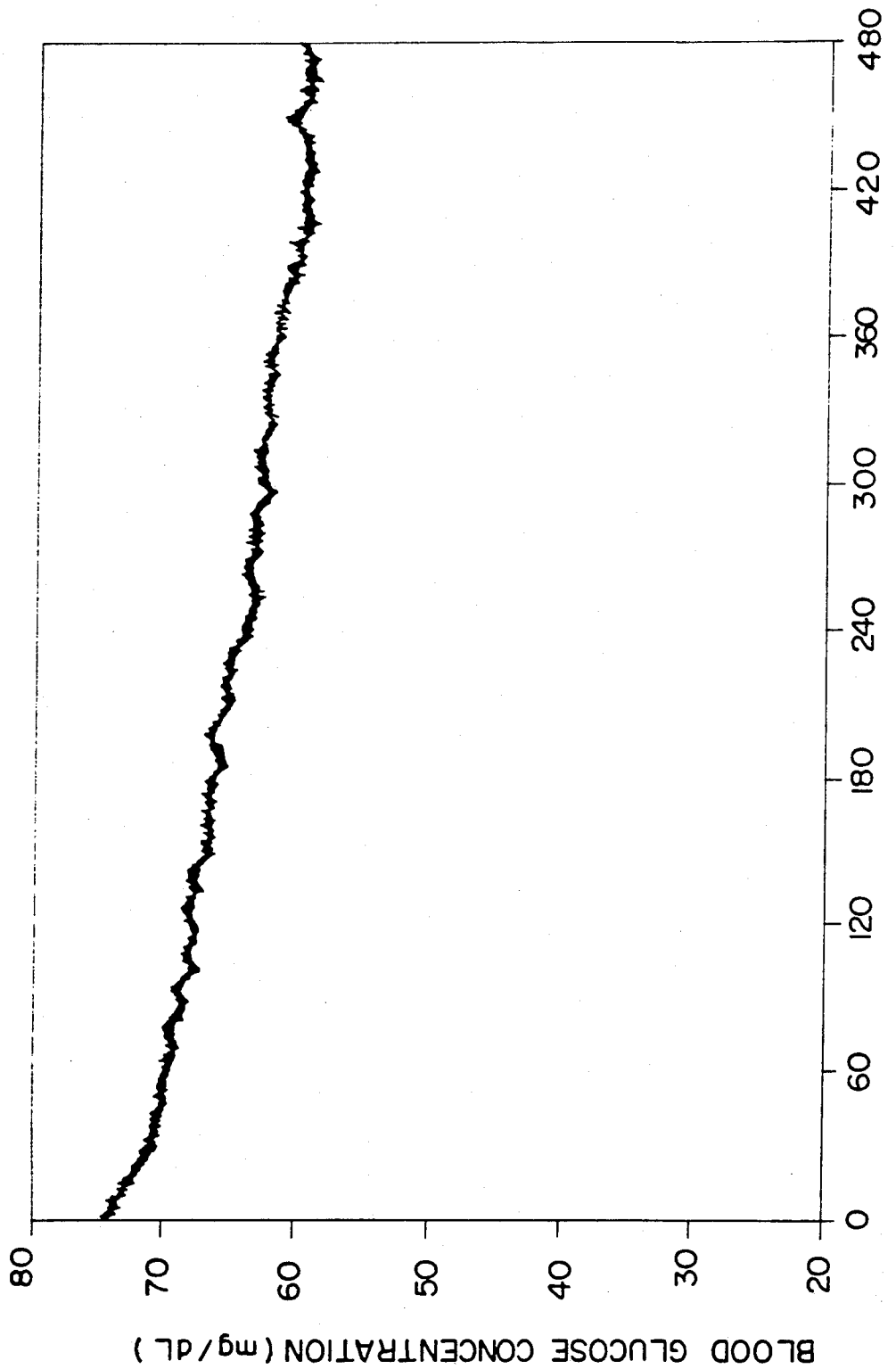
FIG. 11 is a plot of the blood glucose concentration of an animal subject as a function of time after nasal administration of 0.1 ml of an insulin preparation according to Example 12.

The preparations of the comparative examples lacking glycyrrhetinic acid caused an insignificant decrease in blood glucose from 70 mg % to 60 mg % over seven hours. Preparations containing glycyrrhetinic acid and five units of insulin induced marked decreases in blood glucose concentration in only 50 to 50 minutes (FIGS. 1, 2 and 3). The effect was even greater in those animals receiving 10 unit insulin doses (FIGS. 4, 5, 6, 7 and 8).

INSULIN ABSORPTION HUMAN STUDY

Figure 13:
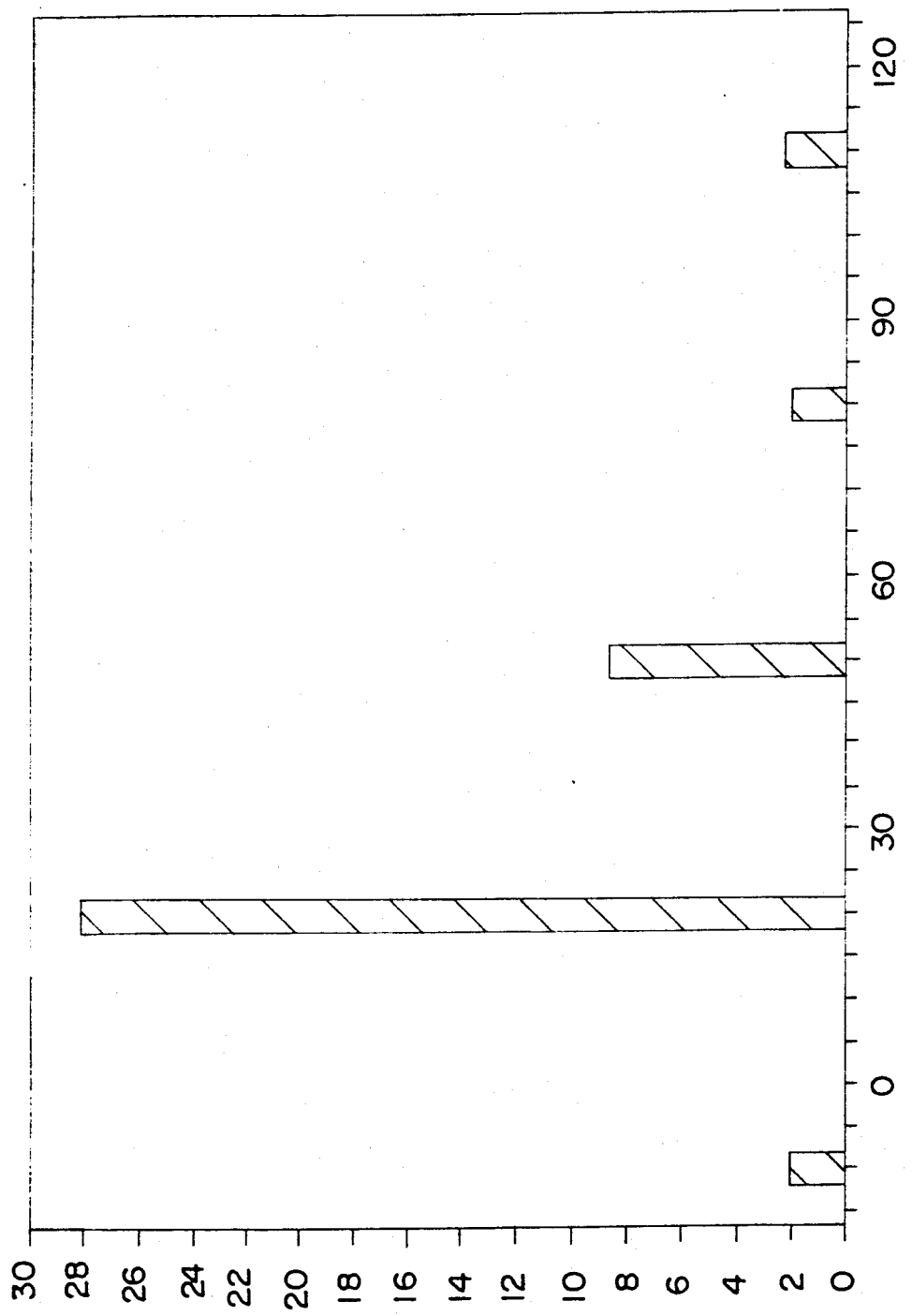
FIG. 13 is a plot of the free insulin blood plasma concentration of a human subject as a function of time just prior to and after nasal administration of 50 units of an insulin composition according to Example 6 utilizing porcine insulin.

A preparation according to Example 6, except for the substitution of a porcine insulin solution of 50 units/ml insulin (Eli Lilly & Co.) for human insulin, was administered to a diabetic patient as follows. The basal free plasma insulin concentration was measured as 2 ng/ml. The patient received a dose of the preparation equivalent to 50 units of insulin at time T=0 from a nasal nebulizer (Pfeiffer Inc., Princeton Jct, N.J.). The tip of the nebulizer was introduced through the nasal aperture. The patient was instructed to inhale as the plunger was depressed, delivering the preparation as a spray of droplets into the upper and inner areas of the nasal cavity. Twenty minutes after administration, the concentration of free insulin in the patient's blood increased to 28 ng/ml. The free insulin level fell to 9 ng/ml 50 minutes after administration, and to the basal level of 2 ng/ml at 80 minutes. See FIG. 13. The patient reported no irritation or stinging.

EXAMPLE 14 - HUMAN GROWTH HORMONE

One ml of a solution containing 100.5 mg sodium glycinate per ml of distilled water was added to 100.3 mg of 18β-glycyrrhetinic acid in a test tube. The mixture was stirred with a glass rod and heated to 90-100° C. in a water bath for about 5 minutes to dissolve the glycyrrhetinic acid. Stirring continued until the mixture became homogeneous. Following removal from the water bath, 1 ml of glycerin was added to the mixture, and water was added q.s. up to 5 ml to form a 2% glycyrrhetinic acid mixture. Then, 1 ml of this 2% glycyrrhetinic acid mixture was mixed with 1 ml of water forming a 1% (w/v) glycyrrhetinic acid preparation. One ml of this preparation was added to 7 mg of human growth hormone ("hGH") to yield a final intranasal preparation of 7 mg/ml hGH.

HUMAN GROWTH HORMONE ABSORPTION ANIMAL STUDY

Five preconditioned female mongrel hound dogs, weighing 19-20 kg and having been treated for worms, were fasted overnight and anesthetized in the morning with intravenous sodium pentobarbital ("NEMBUTAL"; 250 mg initial dose, 25 mg every 30 minutes for maintenance). A medicine dropper was inserted through the nasal opening of each dog into the nasal cavity. A plastic tubing was inserted through the medicine dropper into the nasal cavity. About 0.3 ml of the 7 mg/ml hGH preparation of Example 14 was administered through injection into the plastic tubing with a small syringe. Each animal received a nasal dosage of about 2.1 mg of hGH. Two ml blood samples were withdrawn from the hind paw of each dog with a syringe at the following time intervals (t=0 is the instant of nasal administration of hGH):

t = (min)

−10
−5
5
10
20
30
45
60
75
90
120
150
180

Upon withdrawal, each sample was centrifuged at 60 r.p.m. for 10 minutes. The supernatant (plasma) was decanted to another tube and frozen until analysis.

Figure 14:
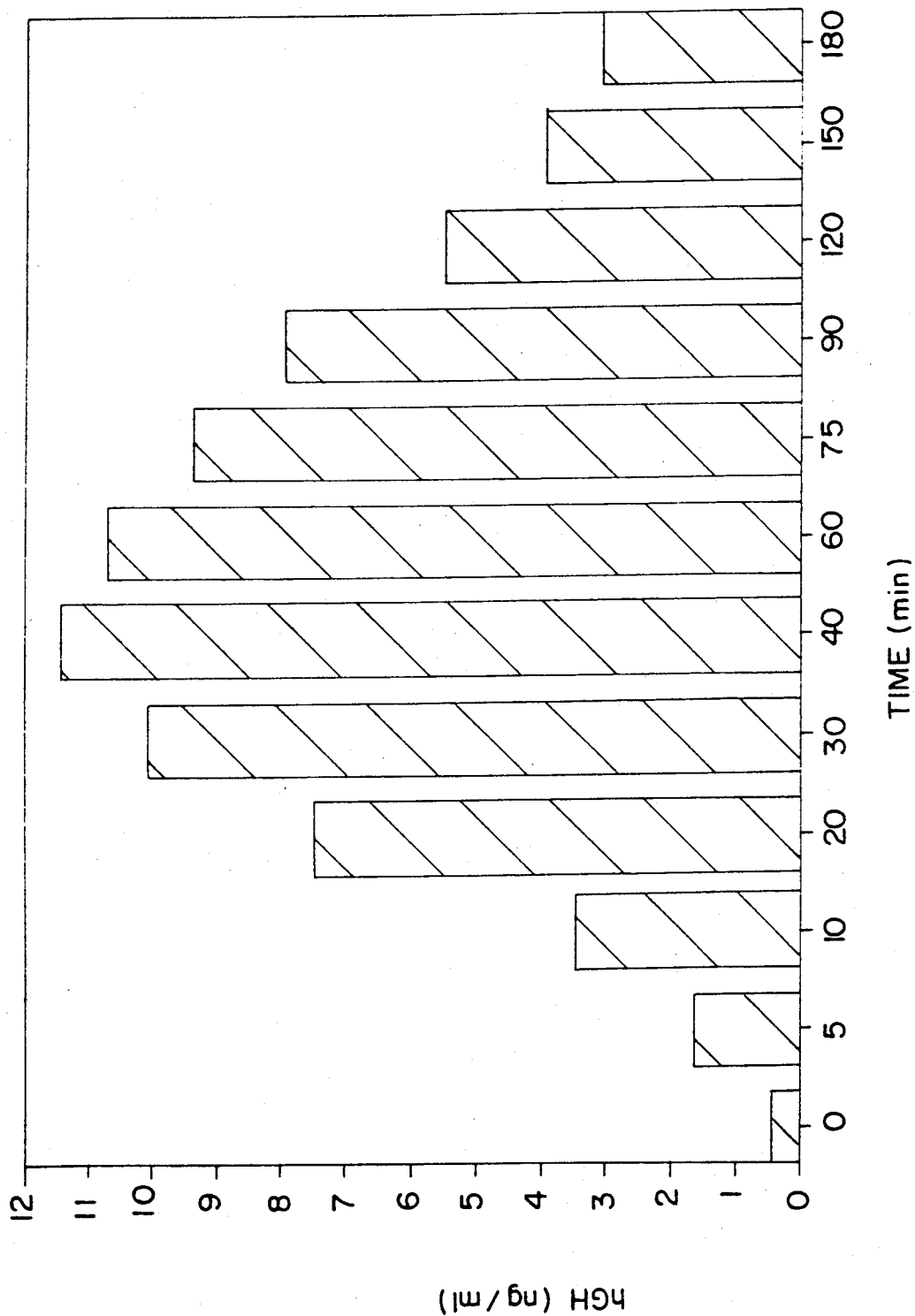
FIG. 14 is a plot of the concentration of human growth hormone in the blood plasma of an animal subject as a function of time after nasal administration of 0.3 ml of a human growth hormone preparation according to Example 14.

The supernatant samples were assayed for growth hormone using a radioimmunoassay procedure for hGH as essentially described in Schalch, et al. "A Sensitive Double Ab Immunoassay for hGH in Plasma," Nature 203:1141 (1964). The results of the radioimmunoassay of the plasma samples, averaged for all five dogs, are summarized in FIG. 14. The data shows that there was a dramatic increase in blood plasma hGH in the animals following intranasal administration.

EXAMPLE 15 — HUMAN GLUCAGON

The intranasal administration of human glucagon is illustrated as follows. Glucagon is an about 3.5 kDa polypeptide which has the opposite effect of insulin, namely, it increases blood glucose.

A 1.0 (w/v) 18β-glycyrrhetinic acid vehicle was prepared as follows. To 100.3 mg of 18β-glycyrrhetinic acid powder in a test tube was added 1 ml of a sodium glycinate solution prepared by dissolving 100.5 mg sodium glycinate in 10 ml of water. The test tube was immersed in a water bath between 80° and 90° C. until the mixture became liquid. The test tube was removed from the bath, and 3 ml of propylene glycol was added. When the solution in the test tube cleared, 0.6 ml of a glycinate-HCl solution (50 mg/ml) was added, followed by water q.s. to 10 ml, to form a 1% (w/v) 18β-glycyrrhetinic acid vehicle.

1 mg of lyophilized glucagon powder was dissolved in 1.0 ml of the above-prepared 1.0% (w/v) glycyrrhetinic acid vehicle and diluted 1:1 with water. 0.2 ml of the resulting solution were intranasally administered to a dog (Dog A) followed by glucose monitoring, according to the procedures set forth in "Insulin Absorption Animal Study", above. The effectiveness of the intranasal absorption of glucagon was indicated by a substantial increase in blood glucose level from a baseline level of 69 mg/dL to 120 mg/dL (Table 2). In comparison, the administration of glucagon dissolved in a commercially-available diluent for glucagon administration (Eli Lily & Co.) (0.2 ml) without glycyrrhetinic acid (Dog B) resulted in substantially no change in blood glucose level ([glucose] = 69 mg/dL baseline, 74 mg/dL max.).

TABLE 2

| | Serum Glucose (mg/dL) | |
|---|---|---|
| Time (min) | Dog A | Dog B (control) |
| 0 | 69 | 68 |
| 5 | 69 | 69 |
| 10 | 80 | 70 |
| 15 | 104 | 72 |
| 20 | 120 | 73 |
| 25 | 111 | 73 |
| 30 | 103 | 72 |
| 35 | 100 | 74 |
| 40 | 90 | 72 |
| 45 | 81 | 71 |
| 50 | 80 | 69 |
| 55 | 62 | 69 |

EXAMPLE 16 — HUMAN ACTH

Human adrenocorticotropic hormone ("ACTH") is a 39 amino acid polypeptide secreted by the anterior lobe of the pituitary gland, which stimulates an increase in the secretion of adrenal cortical steroid hormones, for example, cortisol. The intranasal administration of human ACTH is illustrated as follows.

A 0.5% (w/v) 18β-glycyrrhetinic acid vehicle solution was prepared by diluting the 1.0% (w/v) vehicle of Example 15 1:1 with water. Forty units of ACTH were dissolved in 1 ml the solution. To each nostril of a dog (Dog A) was administered 0.3 ml of the ACTH-containing solution, for a total dosage of 24 units of ACTH. A control dog (Dog B) received, through each nostril, 0.3 ml of a forty unit per ml bacteriostatic solution of ACTH lacking glycyrrhetinic acid. The effectiveness of the preparations was followed by serum cortisol monitoring essentially according to the method of Beitin et al., Steroids 15, 765-776 (1970). The results are set forth in Table 3. While the serum cortisol level reached a peak of only 12.1 µg/dL at time t=30 minutes in the control animal, the serum cortisol concentration in the animal receiving ACTH in a glycyrrhetinic acid vehicle reached 15.3 µg/dL by the same time interval, indicating the nasal absorption enhancing effect of the glycyrrhetinic acid vehicle.

TABLE 3

| Time (min) | Serum Cortisol (µg/dL) | |
|---|---|---|
| | Dog A | Dog B (control) |
| −15 | 6.4 | 7.2 |
| 0 | 3.6 | 3.8 |
| 15 | 12.6 | 11.8 |
| 30 | 15.3 | 12.1 |
| 45 | 7.4 | 10.9 |
| 60 | 6.5 | 7.2 |
| 90 | 3.8 | 5.0 |
| 120 | 2.9 | 4.0 |
| 150 | 2.7 | — |
| 180 | 2.4 | — |

EXAMPLE 17

The intranasal administration of human chorionic gonadotropin hormone (hCG) is illustrated as follows. The hormone is an about 29 kDa glycoprotein, secreted by the placenta.

Twenty thousand units of hCG were dissolved in 4 ml of the same 0.5% (w/v) glycyrrhetinic acid vehicle utilized in Example 16 A total of 0.9 ml in 0.3 ml doses were intranasally administered to a Dog A (total dosage = 4500 units hCG). A control animal (Dog B) received the same amount of hCG in a diluent (sodium chloride physiological solution) lacking glycyrrhetinic acid. The effectiveness of the preparation was determined by serum hCG radioimmunoassay. As shown in Table 4, the serum hCG level remained at the baseline level of below 3 milliunits per ml in the control dog, while attaining a peak level of 18 milliunits in 30 minutes in the animal receiving hCG in the glycyrrhetinic acid vehicle.

TABLE 4

| Time (min) | Serum hCG (milliU/ml) | |
|---|---|---|
| | Dog A | Dog B (control) |
| −15 | <3 | <3 |
| 0 | <3 | <3 |
| 15 | 12 | <3 |
| 30 | 18 | <3 |
| 45 | 17 | <3 |
| 60 | 17 | <3 |
| 80 | 11 | <3 |
| 100 | 10 | <3 |

EXAMPLE 18

The intranasal administration of vitamin B-12 is illustrated as follows.

1 ml of a vitamin B-12 solution containing 1,000µg/ml was mixed with 1 ml of the same 0.5% (w/v) glycyrrhetinic acid vehicle utilized in Example 16. A total of 0.9 ml in 0.3 ml doses was intranasally administered to a dog (Dog A) weighing approximately 40 pounds. A second vitamin B-12 sample (1,000µg/ml) was combined with 1 ml of distilled water and administered intranasally to a control dog (Dog B) in three 0.3 ml doses. Serum B-12 level were measured for each dog by radioimmunoassay. As shown in Table 5, serum B-12 levels increased in the control dog from a baseline level of 229 picogram/ml to approximately 4,000 picograms/ml over the course of 150 minutes. In contrast, the animal receiving the vitamin in glycyrrhetinic acid vehicle attained a peak serum B-12 concentration of over 22,000 picograms/ml in only 15 minutes.

TABLE 5

| Time (min) | Serum Vitamin B-12 | |
|---|---|---|
| | Dog A | Dog B (control) |
| −15 | 255 | 229 |
| 0 | 6248 | 847 |
| 15 | 22263 | 2381 |
| 30 | 18363 | 2225 |
| 45 | 17854 | 3229 |
| 60 | 12471 | 3535 |
| 90 | 9467 | 3658 |
| 120 | 6853 | 3973 |
| 150 | 5479 | 3988 |

The present invention may be embodied in other specific forms without departing from the spirit or essential attributes thereof and, accordingly, reference should be made to the appended claims, rather than to the foregoing specification, as indicating the scope of the invention.

CLAIMS

1. In a composition for the intranasal administration of a pharmaceutically active substance containing an effective amount of said pharmaceutically active substance, the improvement comprising the inclusion of glycyrrhetinic acid in an amount effective for enhancing permeation of said active substance across the nasal membrane, and a basic salt of an amino acid as an adjuvant.

2. A composition according to claim 1 wherein the glycyrrhetinic acid comprises 18α-glycyrrhetinic acid, 18β-glycyrrhetinic acid, or mixtures thereof.

3. A composition according to claim 2 wherein the amino acid basic salt is selected from the group consisting of sodium and potassium salts of glycine, aspartic acid and glutamic acid.

4. A compound according to claim 2 further containing a polyhydric alcohol.

5. A composition according to claim 4 wherein the polyhydric alcohol comprises glycerin.

6. A composition according to claim 4 wherein the polyhydric alcohol comprises propylene glycol.

7. A composition according to claim 2 containing from about 0.25% (w/v) to about 1.5% (w/v) glycyrrhetinic acid.

8. A composition according to claim 7 containing from about 0.5% (w/v) to about 1.0% (w/v) glycyrrhetinic acid.

9. A composition according to claim 2 containing from about 1 to about 5 moles of amino acid basic salt per mole of glycyrrhetinic acid.

10. A composition according to claim 2 wherein the pharmaceutically active substance comprises a peptide or a polypeptide.

11. A composition according to claim 10 wherein the pharmaceutically active substance comprises insulin.

12. A composition according to claim 10 wherein the pharmaceutically active substance comprises growth hormone.

13. A composition according to claim 10 wherein the pharmaceutically active substance comprises glucagon.

14. A composition according to claim 10 wherein the pharmaceutically active substance comprises adrenocorticotropic hormone.

15. A composition according to claim 10 wherein the pharmaceutically active substance comprises chorionic gonadotropin.

16. A composition-according to claim 2 wherein the pharmaceutically active substance comprises vitamin B-12.

17. An aqueous insulin solution for intranasal administration comprising an effective amount of insulin, glycyrrhetinic acid in an amount effective for enhancing permeation of said insulin across the nasal mucosa, and a basic salt of an amino acid as an adjuvant for dissolving said glycyrrhetinic acid.

18. An aqueous insulin solution according to claim 17 wherein the glycyrrhetinic acid comprises 18α-glycyrrhetinic acid or 18β-glycyrrhetinic acid, or mixtures thereof.

19. An aqueous insulin solution according to claim 18 wherein the concentration of glycyrrhetinic acid is from about 0.25% (w/v) to about 1.5% (w/v).

20. An aqueous insulin solution according to claim 19 wherein the concentration of glycyrrhetinic acid is from about 0.5% (w/v) to about 1.0% (w/v).

21. An aqueous insulin solution according to claim 20 wherein the glycyrrhetinic acid is 18β-glycyrrhetinic acid.

22. An aqueous insulin solution according to claim 21 additionally containing a polyhydric alcohol in an amount effective to increase the solubility of glycyrrhetinic acid in said composition.

23. An aqueous insulin solution according to claim 22 wherein the amino acid basic salt is selected from the group consisting of sodium and potassium salts of glycine, aspartic acid and glutamic acid.

24. A method for treatment of diabetes mellitus which comprises administering through the nasal mucous membrane of a patient suffering from diabetes an aqueous insulin solution according to claim 17.

25. A method for administering a pharmaceutically active agent which comprises administering such agent by permeation across the nasal membrane of an animal or human in combination with a permeation-enhancing amount of glycyrrhetinic and a basic salt of an amino acid acid.

26. A method according to claim 25 wherein the glycyrrhetinic acid comprises 18α-glycyrrhetinic acid, 18β-glycyrrhetinic acid, or mixtures thereof.

27. A method according to claim 26 for administering insulin.

28. A method according to claim 26 for administering growth hormone.

29. A method according to claim 26 for administering glucagon.

30. A method according to claim 26 for administering adrenocorticotropic hormone.

31. A method according to claim 26 for administering chorionic gonadotropin.

32. A method according to claim 26 for administering vitamin B-12.

* * * * *